US011013426B2

(12) United States Patent
Deshpande et al.

(10) Patent No.: US 11,013,426 B2
(45) Date of Patent: May 25, 2021

(54) SYSTEM AND METHOD OF FUNCTIONAL MRI OF THE NEURAL SYSTEM IN CONSCIOUS UNRESTRAINED DOGS

(71) Applicant: Auburn University, Auburn, AL (US)

(72) Inventors: Gopikrishna Deshpande, Auburn, AL (US); Paul Waggoner, Jacksonville, AL (US); Vitaly Vodyanoy, Auburn, AL (US); Hao Jia, Shanxi (CN); Oleg Pustovyy, Auburn, AL (US); Thomas Denney, Auburn, AL (US); Ed Morrison, Auburn, AL (US); Ronald Beyers, Auburn, AL (US)

(73) Assignee: Auburn University, Auburn, AL (US)

( * ) Notice: Subject to any disclaimer, the term of this patent is extended or adjusted under 35 U.S.C. 154(b) by 1165 days.

(21) Appl. No.: 15/005,660

(22) Filed: Jan. 25, 2016

(65) Prior Publication Data

US 2016/0213279 A1    Jul. 28, 2016

Related U.S. Application Data

(60) Provisional application No. 62/106,848, filed on Jan. 23, 2015.

(51) Int. Cl.
*A61B 5/055* (2006.01)
*A61B 5/00* (2006.01)
(Continued)

(52) U.S. Cl.
CPC ............ *A61B 5/055* (2013.01); *A61B 3/0091* (2013.01); *A61B 3/113* (2013.01); *A61B 5/4011* (2013.01);
(Continued)

(58) Field of Classification Search
None
See application file for complete search history.

(56) References Cited

U.S. PATENT DOCUMENTS 4,234,876 A * 11/1980 Murai .................. A01K 29/005
119/859
2006/0084858 A1* 4/2006 Marks ...................... A61B 5/16
600/407
(Continued)

OTHER PUBLICATIONS

Berns et al., "Functional MRI in Awake Unrestrained Dogs," PLos One, May 2012, 7(5):e38027.
(Continued)

*Primary Examiner* — Oommen Jacob
*Assistant Examiner* — Shahdeep Mohammed
(74) *Attorney, Agent, or Firm* — Christopher M. Scherer; DeWitt LLP (57) ABSTRACT

Many factors contribute to dogs' superior olfactory capabilities as compared to humans. Studies explored this aspect at the cellular and behavior levels; however, the cognitive-level neural substrates linking them have never been explored. Since sedated dogs cannot sniff, the present application illustrates the cognitive-level linking neural substrate using fMRI of conscious dogs. The head motion of the canine is accounted for by behavioral training and optical motion tracking. The olfactory bulb is commonly activated in both awake and anesthetized dogs, while parietal and frontal structures are activated only in the former and subcortical structures only in the latter. Comparison of low and high odor intensity shows differences in both the strength and spatial extent of activation in higher cognitive structures. Unlike humans, neural structures even at the top of the cognitive hierarchy are modulated by odor concentration in dogs. This represents one possible mechanism for their superior sense of olfaction as compared to humans.

5 Claims, 8 Drawing Sheets (51) Int. Cl.
*A61B 3/113* (2006.01)
*A61B 3/00* (2006.01)
*A61B 90/00* (2016.01)

(52) U.S. Cl.
CPC .......... *A61B 5/0035* (2013.01); *A61B 5/0077* (2013.01); *A61B 5/7475* (2013.01); *A61B 2090/3979* (2016.02); *A61B 2503/40* (2013.01)

(56) References Cited

U.S. PATENT DOCUMENTS

2012/0220857 A1   8/2012   Warr
2016/0066838 A1*  3/2016   DeCharms ........... A61B 5/4824
                                                          434/236

OTHER PUBLICATIONS

Lowen SB and Lukas SE. A low-cost, MR-compatible olfactometer. Behavior Research Methods 38,307-313, 2006.†

Cook PF, Spivak M, Berns GS. One pair of hands is not like another. caudate BOLD response in dogs depends on signal source and canine temperament. PeerJ, 2,e596, Sep. 30, 2014.†

Berns GS, Brooks AM, Spivak M. Scent of the familiar. An fMRI study of canine brain responses to familiar and unfamiliar human and dog odors. Behavioural Processes, first appeared online Mar. 6, 2014.†

Gregory Berns, book titled, How Dogs Love Us, published by Amazon New Harvest (New York), Oct. 2013.†

Berns GS, Brooks AM, Spivak M. Functional MRI in awake unrestrained dogs. PLoS One 7(5), e38027, May 11, 2012.†

Berns GS, Brooks A, Spivak M. Replicability and heterogeneity of awake unrestrained canine fMRI responses. PLoS One 8(12),e81698, Dec. 4, 2013.†

Gregory Berns, Dogs are people, too. New York Times Op-Ed, published Oct. 7, 2013.†

Dilks DD, Cook P, Weiller SK, Berns HP, Spivak M, Berns GS. Awake fMRI reveals a specialized region in dog temporal cortex for face processing. PeerJ 3, e1115, Aug. 4, 2015.†

Helen Berns, Do Dogs Recognize Faces. An fMRI Study. Feb. 2014.†

Stallion News, Newsletter for the Sandy Springs Charter Middle School. Feb. 21, 2014.†

* cited by examiner
† cited by third party

SYSTEM AND METHOD OF FUNCTIONAL MRI OF THE NEURAL SYSTEM IN CONSCIOUS UNRESTRAINED DOGS

CROSS-REFERENCE TO RELATED APPLICATIONS

This application claims priority to U.S. Provisional Application No. 62/106,848, filed Jan. 23, 2015, the content of which is incorporated herein by reference in its entirety.

FIELD

The present application relates to the field of canine magnetic resonance imaging (MRI) systems. More specifically, the present application relates to the field of functional magnetic resonance imaging (fMRI) systems of fully awake, conscious and unrestrained dogs to monitor their brain activity in general and response to olfactory system stimulation in particular.

BACKGROUND

Figure 1:
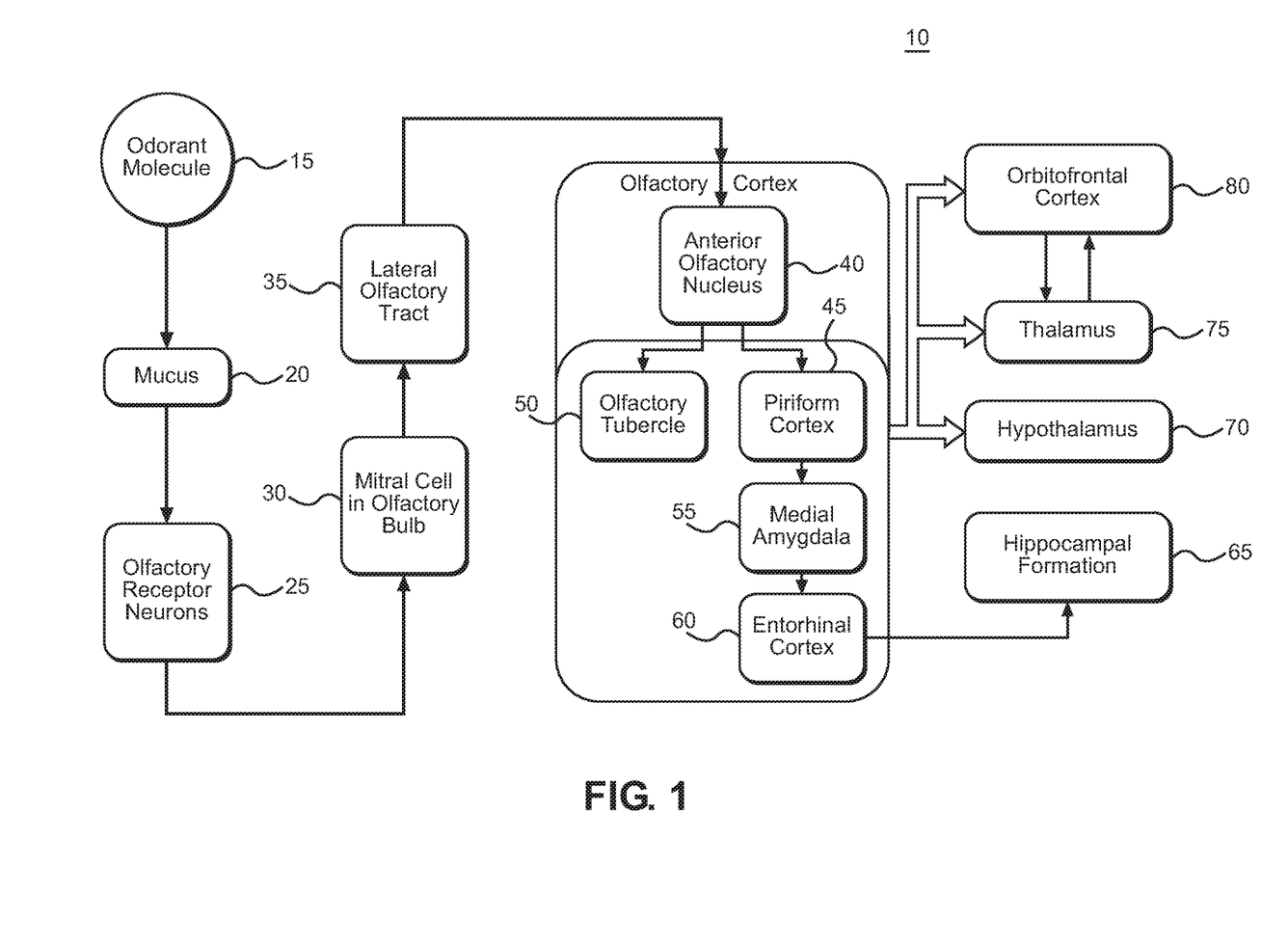
FIG. 1 is a schematic diagram illustrating the olfactory pathway in canines.

Referring to FIG. 1, the properties of the dog's olfactory system 10 results from physical and biochemical events that occur at the olfactory epithelium of the nasal cavity where olfactory receptor neurons interact with odorants. Olfaction begins with sniffing, which transports odorant molecules 15 into the nose and delivers them to the mucus layer 20 covering the olfactory epithelium. The binding of the odorant by a receptor protein initiates an intracellular cascade of signal transduction events, including the G-protein-dependent production of second messenger molecules, leading to opening of ion channels and passing of ion currents. This process triggers an action potential in the olfactory receptor neuron 25 axon that projects directly to the olfactory bulb (OB) 30. OB neurons transmit signals along a lateral olfactory tract 35 to pyramidal neurons in the olfactory cortex 40 that is composed of the piriform cortex 45, olfactory tubercle 50, anterior olfactory nucleus, the medial amygdala 55 and entorhinal cortex 60. The pathway then projects to the hippocampal formation 65, hypothalamus 70, and thalamus 75, which relays information to neocortical areas such as the orbitofrontal cortex 80 where the olfactory signal is interpreted. Previous studies have shown that dogs possess a hundred times more olfactory receptors 25 per square centimeter as compared to humans. This clearly demonstrates the dogs' advantage over humans in sensory transduction at the cellular level. However, how this advantage is carried forward higher into the odorant detection chain remains unexplored.

While much is known about the canine olfactory system at the in vitro cellular level and behavioral level, little work has been done at the cognitive level, which is an important and largely unexplored link in series of events leading to odor detection. It is critical to bridge the gap between cellular findings and systemic behavioral observations by investigating the sense of smell at the cognitive level. For example, an increase in the concentration of odorant will induce a change in response at the cellular level according to Weber's law. How this change in response translates to a change in odorant detection in vivo, however, is unknown.

Also, head movement is a critical issue for all modalities of brain imaging, especially for fMRI. Excessive movement results in image ghosting and blurring. Because head movement is a significant obstacle in imaging studies of conscious animals, and some cognitive processes such as olfaction are impossible to comprehensively study in anesthetized animals, the system of the present application is an approach involving both dog training and optical head motion tracking. Even the best trained dogs will inevitably make slight, sometimes jerky, head movement. In the present case, the dogs would sometimes pant, which is a physiologically mediated response that is difficult to reliably control through positive reinforcement procedures. Such motions are difficult to remove using post-hoc image transformations. Therefore, the ability to compensate or reduce motion artifacts is one of the most challenging difficulties while acquiring MR images from a conscious animal. To solve this problem, the head of the animal may be immobilized using external constraints. But this method makes the animal uncomfortable and hence the data collected is not fully ecologically valid; furthermore, such restraint is aversive and considered to be a higher level of invasiveness from an animal welfare point of view.

SUMMARY

Many factors contribute to dogs' superior olfactory capabilities as compared to humans. Studies explored this aspect at the cellular and behavior levels; however, the cognitive-level neural substrates linking them have never been explored. Since sedated dogs cannot sniff, the present application illustrates the cognitive-level linking neural substrates using fMRI of conscious dogs. The head motion of the canine is accounted for by behavioral training and optical motion tracking. The olfactory bulb (OB) is commonly activated in both awake and anesthetized dogs, while parietal and frontal structures are activated only in the former and subcortical structures only in the latter. Comparison of low and high odor intensity shows differences in both the strength and spatial extent of activation in higher cognitive structures. Unlike humans, neural structures even at the top of the cognitive hierarchy are modulated by odor concentration in dogs. This represents one possible mechanism for their superior sense of olfaction as compared to humans.

In one aspect of the present application, an olfactory stimulation device for use in an olfactory imaging system comprises an inflow air path, wherein the inflow air path controls the delivery of a pre-determined quantity of an odorant to an animal through a mask over a pre-determined time interval, a clearance air path, wherein the clearance air path controls the removal of the pre-determined quantity of odorant at the end of the pre-determined time period, and a controller and a timer, wherein the controller and timer effectuate the operation of the inflow air path and the clearance air path.

In another aspect of the present application, a head motion tracking system for use in a functional magnetic resonance imaging (fMRI) scanner comprises a dot reflector mounted to a head of a subject of the scanner, an infrared (IR) illuminator, wherein the IR illuminator provides an IR source that is directed toward the head of the subject, and an IR camera, wherein the IR source is reflected by the dot reflector, and further wherein the IR camera receives the IR source as an image, and a change in position of the dot reflector is calculated, wherein the IR camera binarizes the image in order to separate the dot reflector from the subject and other background, and a computing device is utilized to calculate the change in position of the dot reflector.

In another aspect of the present application, a system for exposing a dog subject of a functional magnetic resonance imaging (fMRI) to human emotional images and for tracking the eyes of the dog subject during the fMRI comprises the fMRI system including a scanner, a screen mounted above the scanner and beyond a rear end of the scanner such that a head of the dog subject is placed in a head coil located at the rear end of the scanner, and an eye tracking device configured such that the eye tracking device confirms that the eyes of the dog subject remain looking at the screen during the fMRI, wherein a set of emotional human face images is projected on the screen during the fMRI.

DETAILED DESCRIPTION OF THE DRAWINGS

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

The system and method of the present application may be effectuated and utilized with any of a variety of computers or other communicative devices, exemplarily, but not limited to, desk top computers, laptop computers, tablet computers, or smart phones. The system will also include, and the method may be effectuated by a central processing unit that executes computer readable code such as to function in the manner as disclosed herein. Exemplarily, a graphical display that visually presents data as disclosed herein by the presentation of one or more graphical user interfaces (GUI) is present in the system. The system further exemplarily includes a user input device, such as, but not limited to, a keyboard, mouse, or touch screen that facilitate the entry of data as disclosed herein by a user. Operation of any part of the system and method may be effectuated across a network or over a dedicated communication service, such as land line, wireless telecommunications, or LAN/WAN.

The system may further include a server that provides accessible web pages by permitting access to computer readable code stored on a non-transient computer readable medium associated with the server, and the system executes the computer readable code to present the GUIs of the web pages.

Embodiments of the system can further have communicative access to one or more of a variety of computer readable mediums for data storage. The access and use of data found in these computer readable media are used in carrying out embodiments of the method as disclosed herein.

While much is known about the canine olfactory system at the cellular and behavioral levels, little work has been done at the cognitive level, which is an important and largely unexplored link in the odorant detection network of dogs. On the other hand, fMRI of the olfactory system has been performed in humans and other animals such as monkeys. In dogs, previous imaging has largely been on audio or visual processing. Canines are used extensively for detecting odors in both civilian and national security context, and as service animals. Therefore, in order to bridge the knowledge gap of the dog olfactory system at a cognitive level, the system and method of the present application controls delivery of odorant stimulus to both awake and lightly anesthetized dogs. The system and method of the present application illustrates the feasibility of obtaining fMRI data from the brains of lightly anesthetized and awake dogs receiving odorant stimulus, and the effects of low and high concentrations of odorant and the effect of anesthesia are compared.

Furthermore, a device for the precise controlled delivery of pre-determined quantities of substances over a precise time interval is disclosed. The device is particularly useful for the automatic application or dispensing volatile and non-volatile odorants, fragrance compounds, aromixes and the like to the nasal and phyryngeal cavities of animals and man. The substances can be delivered in vapor or liquid form. The device may also be used to deliver substances to man or animals undergoing a variety of diagnostic tests including but not limited to MRI, Ultrasound, CT scans, nuclear medicine scans, X-ray analyses and the like. The device may also be used to control the imaging device by initiating or terminating the scans at precise times and intervals.

The device provides for the flow of air under pressure through a series of filters, valves, and manifolds to sweep the headspace over containers into a mask or for the precise quantitative delivery of odorants to the nasal/phymgeal cavity of animals or man. A vacuum system then removes the odorant after a precise amount of time. In this manner, the device controls the precise extent and time of exposure of substances to olfactory tissue. The moisture content of the air is controlled to a constant humidity by a dry-rite type air filter. The device also contains an electrical system which utilizes a series of switches, valves, controllers, timers, visual LED channels to control the movement of the odorants to the nose and engaging the diagnostic equipment such as an MRI unit. A cooling fan helps to maintain temperature of substances and device components.

Overview of the fMRI Olfactory Imaging System

The components of the fMRI olfactory imaging system 100 are illustrated. First, the dogs are trained to insert and keep their heads as still as possible inside a human knee coil (FIG. 5) when being scanned. Such training is achieved by positive reinforcement training techniques using a target stick and bridging stimulus, such as a clicker, for head placement maintained by delivery of edible treats for emission of desired responses. An odorant applicator 110 is used for controlled delivery of odorant stimulus. The odorant application will be described in greater detail below. The system 100 includes a scanner 120, one example being a 3T Siemens Verio scanner or other such scanners known in the art, and a human knee coil (FIG. 5) which act as a dog head coil. Of course, a dog head coil may be specially developed for this purpose. An optical head motion tracking system was employed for tracking dog head motion during fMRI, and includes an infrared (IR) camera 135, an IR illuminator 140 (FIG. 2), a video monitor 145, and a data recording palmtop 130. A schematic of the interlinking and triggering among the elements of the system 100 are shown in FIG. 2.

Figure 2:
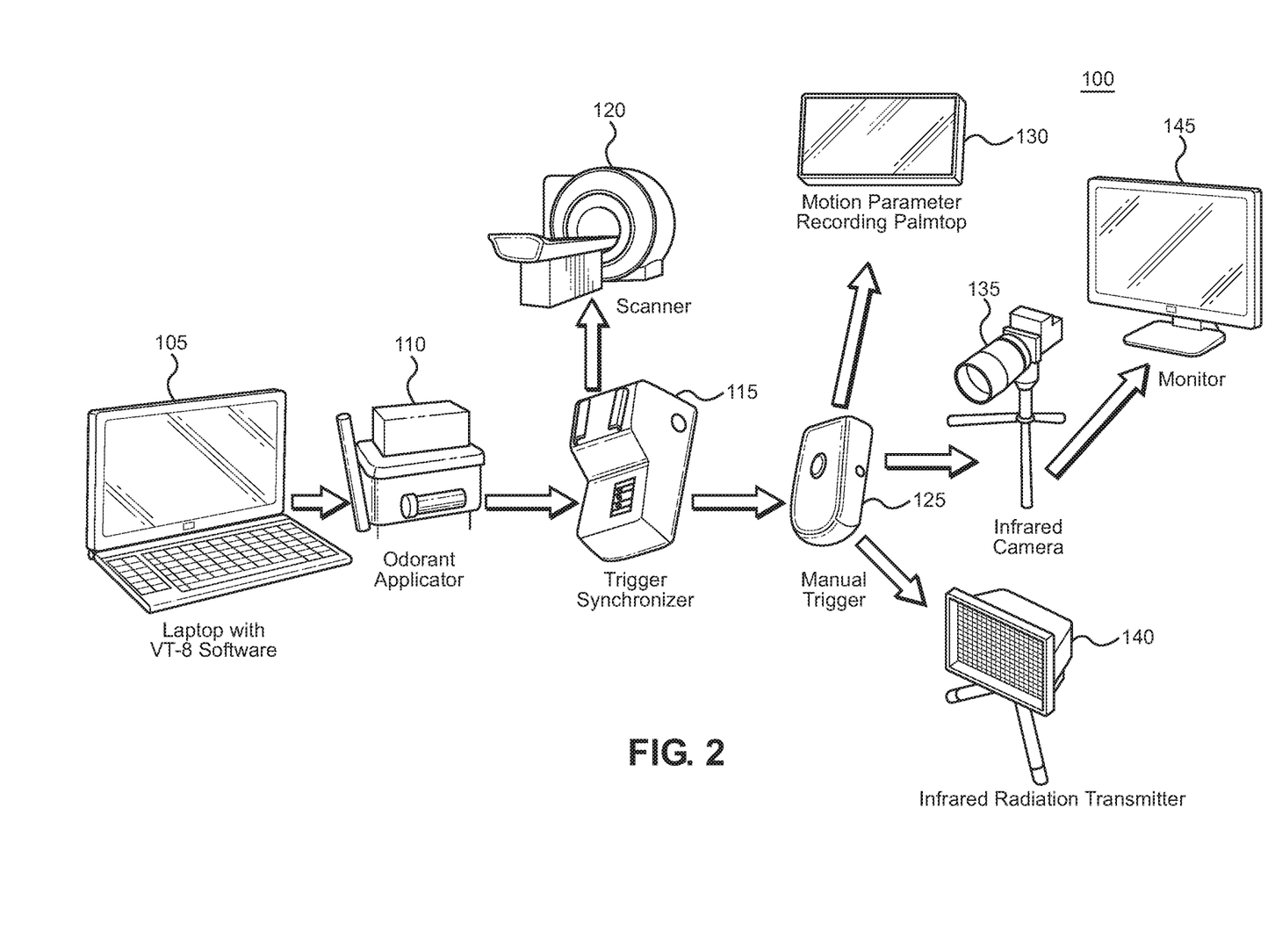
FIG. 2 is schematic diagram illustrating an embodiment of a system of the present application.

Still referring to FIG. 2, arrows denote the triggering direction of the system 100. A laptop or other computing device 105 with VT-8 software provides an interface to trigger the odorant applicator 110. The VT-8 software (or software functionally equivalent) is a platform that can be used to design and display sequence of odorant flow and clearance, and provides communication and control to the odorant applicator 110 to generate the expected sequence. Once the odorant applicator 110 starts to give odorant stimulus, it sends a signal to the trigger synchronizer 115, which then triggers the scanner 120 and sends a signal to the manual trigger 125. The manual trigger 125, as the name suggests, is manually set for switching between two states. One is waiting for signals from trigger synchronizer 115, and the other is waiting for a signal from a hand-pressed button. In one embodiment, the first state is used for data collection and the second state is used only for testing. Upon receiving the signal, the manual trigger 125 triggers the infrared radiation transmitter 140 to give off infrared rays, and the infrared camera 135 to start recording infrared reflections from the dog's head, and the motion parameter recording palmtop 130 to start calculating displacement parameters. When the camera 135 is triggered, it sends the signal to the monitor 145 for display.

Dog Training and Preparation

For anesthetized imaging, dog subjects are sedated with preferably intramuscularly administered xylazine (2.2 mg/kg) and lightly anesthetized with ketamine HCl (11 mg/kg). For awake imaging, the dogs are trained to move to the correct position within the scanner 120, insert their heads within a human knee coil (FIG. 5), and remain still for the required duration of imaging using positive reinforcement behavior shaping procedures as discussed above.

A dog is trained using positive reinforcement to obtain the desired performance. Prior to training for fMRI scanning, the dogs are trained to follow, touch, and remain touching the end of a "target-stick" with their nose using small bits of commercial dog food treats as rewards to shape and maintain this response. Concomitantly, a tin clicker is established as a conditioned reinforcer by pairing the click with the delivery of food treats for correctly touching and holding their nose to a touch-stick. Such a conditioned reinforcer is also known as a "bridge" as it provides an immediate signal to the animal that the desired response has been emitted and bridges the gap in time until a food treat can be delivered. This sort of target-stick and bridging signal training is a common practice in pet animal as well as professional husbandry with animals in zoos to train them to present themselves for medical monitoring and treatment, conduct educational/entertainment animal shows, and to generally reduce the dangers associated with managing animals. The use of the clicker allows more precise delivery of a rewarding stimulus to shape, build, and/or develop a desired response.

Training for awake, unrestrained fMRI dogs is done outside of the actual scanning using a fixture to replicate the human knee coil, for example, using a 2.5 gal plastic bucket with the bottom cut out, affixed to one end of a table that approximates the height and width of the MRI table. The dogs are prompted to jump up on the table or, if unable to easily jump on the table, place their front paws upon the edge of the table so they could be easily lifted upon the table by one person. The previously established clicker and target-stick repertoire is used to train the dog to place its head within the simulated MRI coil and position its nose within the olfactory stimulus delivery mask, which is affixed inside the simulated human knee coil. The dogs are trained to hold their heads relatively motionless within the simulated coil by clicking the clicker only when their head is in the correct position and held still. The amount of time that a dog has to hold its head still in the correct position to receive the click followed by a food treat is gradually increased. Meanwhile, throughout this process, a high-fidelity recording of the sound from the operation of the MRI is played through a portable stereo, the volume of which is gradually increased until similar in intensity to that of being in the actual scanning. The final training performance is the dog holding its head relatively motionless in the correct position while the MRI sounds are played at approximately the same intensity as that of being in the actual MRI for 5 minutes and repeating this performance several times across the course of an hour-long training session.

The awake dogs are then further trained inside the real scanner with the human knee coil and while running of the functional and structural MRI-pulse sequences. The dogs are acclimated and transitioned to performing the head positioning response in the actual MRI scanner. The dog trainer always accompanies and monitors the dog in the scanning room. The dog is prompted onto the MRI table, into the MRI core, to place its head within the human knee coil, and to position its nose in the olfactory stimulus delivery mask. Starting with a relatively short duration of holding its head in position and relatively motionless with the fMRI operating, the time requirement for receiving a click followed by a food treat is variably and rapidly increased until the dog reliably executes the performance for one fMRI sequence to be used in the experiment. The click is presented at the end of the MRI pulse sequence followed by delivery of the food treat from the hand of the trainer to the dog. Even with training, some head movement is inevitable, for example, for respiratory repositioning. Therefore, a single camera optical head motion tracker is used to monitor the motion of the dog's head and retrospectively correct for motion effect.

Olfactory Stimulus Device

The accurate delivery of odor stimulus is very important in olfactory physiological systems. When used with fMRI, demanding additional constraints are placed on olfactometers. The most obvious constraint is the absence of any magnetized material in the MRI room. Other features of the instrument include computer control and odorant presentation of accurate and reproducible duration of a preselected sequence with no additional stimulation, for example, no tactile and/or auditory stimulation.

Figure 3:
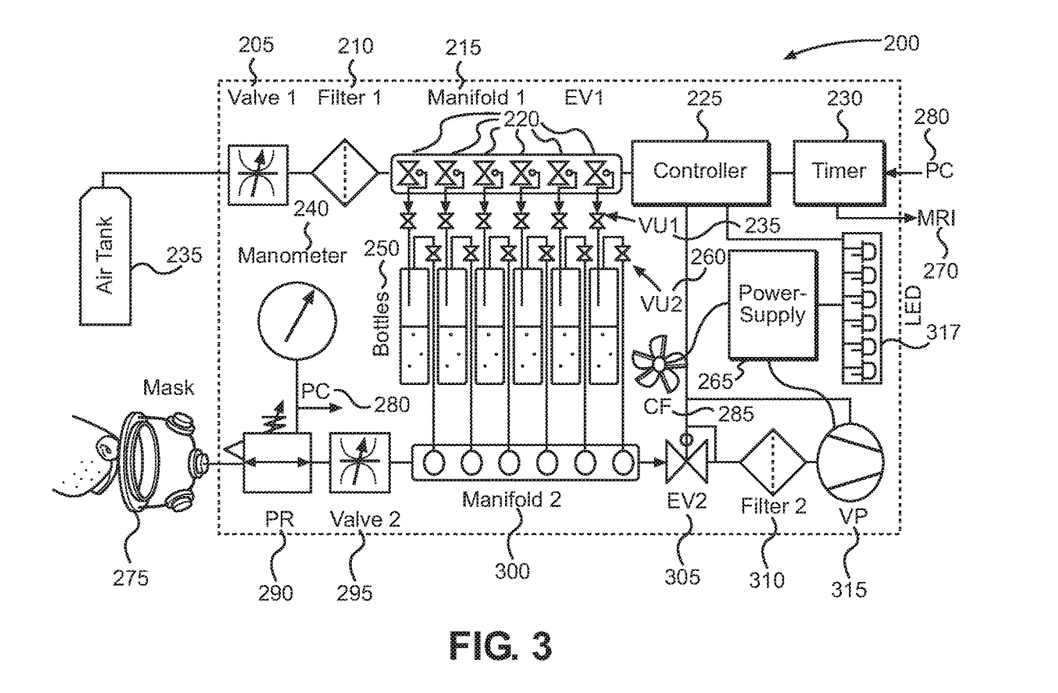
FIG. 3 is a schematic diagram illustrating an embodiment of the system of the present application.

Referring to FIG. 3, the olfactory stimulation device 200 (or odorant applicator 110 of FIG. 2) provides for the precise computer-controlled delivery of pre-determined quantities of odorants over a precise time interval. The device 200 further provides for the flow of air under pressure through a series of filters (210, 310), valves (205, 295, 215, 220, 235, 260, 290, 295, 305, 315), and manifolds (215, 300) to sweep the headspace over containers into a mask 275, for the precise quantitative delivery of odorants to the nasal cavity of the subject dog. A vacuum suction then clears the odorant after a precise amount of time. In this manner, the device 200 controls the precise extent and time of exposure of substances to olfactory tissue. The moisture content of the air is controlled to a constant humidity using preferably a drierite type air filter (210, 310). The drierite type air filter is a purifier that is specially designed for gas chromatography and other applications requiring pure and dry gas. It dries, purifies, and filters gases used for chromatography and spectrometry.

As noted above, the odorant applicator 110 of FIG. 2 is the general name for the device that delivers the odorant to the subject dog in the scanner 120. The olfactory stimulation device 200 illustrated in FIG. 3 is the solution of the illustrated embodiment of the odorant applicator 110 of the present application. It should be understood that in addition to the olfactory stimulation device 200, other solutions and versions of the odorant applicator may be utilized and developed.

The olfactory stimulation device 200 includes inflow & clearance air paths and an electronic control system or controller 225 and timer 230. The inflow air/odorant path includes in one embodiment a tank 235, flow control Valve 1 205, dry-rite type air Filter 1 210, Manifold 1 215, including 6 isolated channels with electronically controlled valves, an electronic valve EV1 220, 6 unidirectional pressure controlled valves (VU1, VU2) 235, 260, 6 odor bottles 250, Manifold 2 300, including 6 flow-through isolated channels), flow control Valve 2 295, pressure regulated valve (PR) 290, and electronic Manometer 240. The clearance path includes vacuum pump (VP) 315, charcoal Filter 2 310, and electronic valve (EV2) 305. The electronic control system includes a 6-channel valve Timer 230, 6-channel valve Controller 225; Power-supply 265 that feeds the VP 315, the visual LED control panel 317, and the cooling fan (CF) 285. Power for the Timer 230 and Controller 225 comes from the personal computer (PC) 280. The protocols of timing and sequencing are stored and directed by the PC 280 connected to the Timer 230, and the Timer 230 is synchronized with the MRI. The air pressure directed to the Mask 275 is measured by the electronic Manometer 240 and recorded by PC 280.

Referring to FIG. 2 and FIG. 3, during fMRI, in one embodiment the air tank 235, odorant applicator 110, 200, and computer 105 280 are positioned outside the MRI room in close proximity to the utility entrance port into the MRI room. Six 6-mm plastic tubes pass through the entrance port for connection with the animal mask 275. Each tube, channel, and bottle was used only for the particular odorant sample to avoid cross contamination. Valve 2 295 and pressure regulator (PR) 290 are purged and cleaned after each session. All materials and components used in this device were chemically stable and are not odoriferous.

As further illustrated in FIG. 2 and FIG. 3, the PC 105, 280 uses VT-8 software to send a signal to the VT-8 Warner Valve Timer 230 that in turn communicates with the VC-8 Warner Valve Controller 225 to open one of six Oxygen Clean 2-way normally closed electronic valves (EV1) 220 installed in the 6-port Oxygen Clean Manifold 1 215. When EV1 220 is open, the corresponding LED 32 control light is on, and air enters from the Air Tank 235 into the Miniature Clippard Air Flow Control Valve (Valve 1) 205. Then through the W.A. Hammond Drierite Laboratory Gas Drying Unit (Filter1) 210 the air travels to the open EV1 220, the first Clippard Unidirectional Valve (VU1) 235, the head space of 100 mL bottle 250, and then the second Clippard Unidirectional Valve (VU2) 260. After that, it follows through the corresponding normally open channel of the Clippard Manifold 2 300 and via the second Miniature Clippard Air Flow Control Valve (Valve 2) 295 to the Clippard Pressure Regulator (PR) 290, with air pressure measured by DT-8890CEM Ruby-electronics Digital Differential Air Vapor Pressure Meter Gauge Manometer 240. Finally, the air with odorant exits the odor applicator and enters the SurgiVet Pet Oxygen Mask 275 via the 6-mm tubing.

It should be noted that any of proper names, or specific manufacturer model names used for any of the components in this olfactory stimulation device 200, or any other portion of the system 100 of the present application, should be taken to mean that the particular model is a component that can be implemented for that particular element of the system 100 of the present application, and that other specific components may be used as long as they function in the same or similar fashion as those listed Still referring to FIG. 3, at the end of activation time, in one embodiment 10 seconds, the Controller 225 closes EV1 220 in the Manifold 1 215 and simultaneously opens the Oxygen Clean 2-way normally closed electronic valve (EV2) 305 and the vacuum pump (VP) 315 in the applicator exhaust path. The air with odorant is cleared from the Mask 275, Valve 2 295, the open channel of Manifold 2 300, EV2 305, and Filter 2. After the clearance of odorant, approximately 10 s, the EV2 305 and the vacuum pump 315 are shut off and the system rests 20 s in one embodiment before a new activation begins. The full cycle of the olfactory stimulation device 200, therefore, is typically composed of 10 s of odor application and 30 s of no odor. The no odor time includes 10 s clearance of odorant and 20 s rest time.

It should further be noted that the duration of the odor applications and clearance of odorant and rest time are depicted in this embodiment to be 10 s, 10 s and 20 s, respectively. However, it will be understood by one skilled in the art that further embodiments of the present application will include adjusted versions of these times as appropriate for the particular application. For example, different types and sizes of dogs may require an adjustment of these times. Also, varying equipment may also cause these timeframes to be adjusted accordingly.

Figure 4:
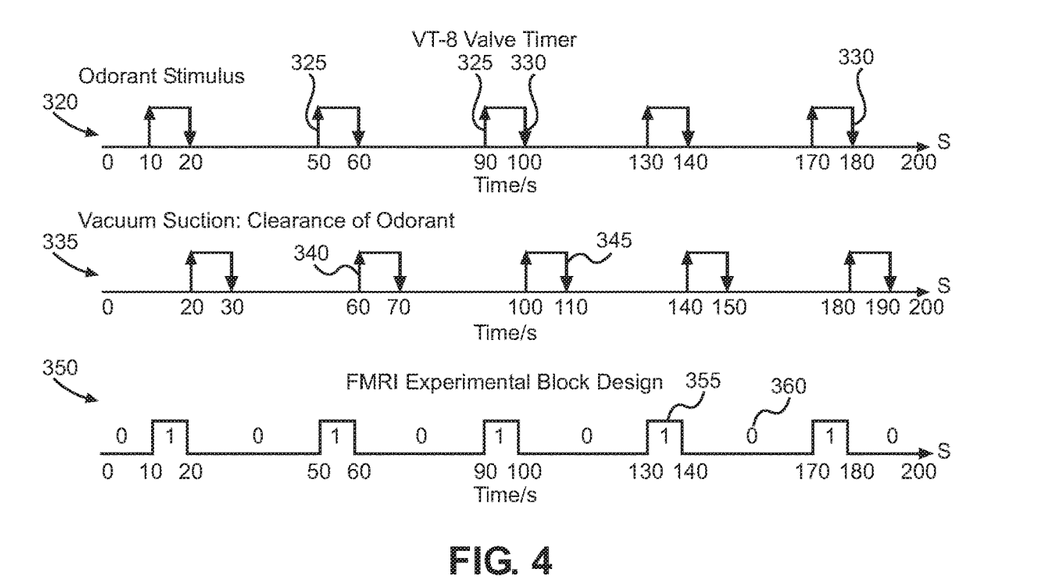
FIG. 4 is a graphical representation of odorant stimulus over time in an embodiment of the system and method of the present application.

Referring now to FIG. 4, a graphical representation of the odorant stimulus and vacuum over time is illustrated. Each of the graphical representations is shown along the x-axis by time in second. The odorant applicator sequences controlled by the Timer 230 software are shown in graphs 320 and 335, and the fMRI experimental block design is shown in graph 350. For the odorant stimulus sequence in graph 320, arrows 325 indicate the onset time of the odorant stimulus and the down arrows 330 indicate when the stimulation ends. In the vacuum suction graph 335, the up arrows 340 indicate the onset of clearance of odorant, and the down arrows 345 indicate when it ends. The graph 350 illustrates the fMRI block design in this embodiment, matching the first sequence, where "0" and "1" denote the odor "on" 355 and "off" 360 conditions.

Referring to FIGS. 2-4, the pressure pulses 355 were measured by the Manometer 240 and sent to the PC 280. The odor applicator (110, 200) is synchronized with the MRI scanner 120 by the Timer 230 signal sent to the PC 280. The cooling fan (CF) 285 maintains the temperature of the odorants and the device 200 components. In this embodiment, a known odorant mixture of ethyl butyrate, eugenol, and (+) and (−) carvone in water at concentrations of 0.016 mM (low concentration) and 0.16 mM (high concentration) each was used.

Referring again to FIG. 3, the odorant applicator (180, 200) is controlled by the software 105, 280 and is programmed to generate the experimental sequence of odorant flow and clearance illustrated in FIG. 4. Since the odorant airstream was unwarmed and introduced at room humidity, excessive flow rate is not desirable. Furthermore, animals subjected to continuous unhumidified flows may have nasal drying and discomfort. High air flow can present air flow turbulence, impacting rise times. Because the mask 275 has two valves that support unrestricted exhaling and inhaling, the incoming air flow should be limited to approximately 1 l/min based on American Animal Hospital Association (AAHA) guidelines.

In this embodiment, the mask 275 is a SurgiVet Pet Oxygen Mask. This mask 275 is made of polycarbonate and has two valves that aid unrestricted exhaling and inhaling, and a port to which the tube for odorant delivery and evacuation is attached. The mask 275 may be mounted on the frame of the knee coil such that when the dog places its nose in the mask, its head is correctly positioned within the coil for imaging, as illustrated in FIG. 5.

Figure 5:
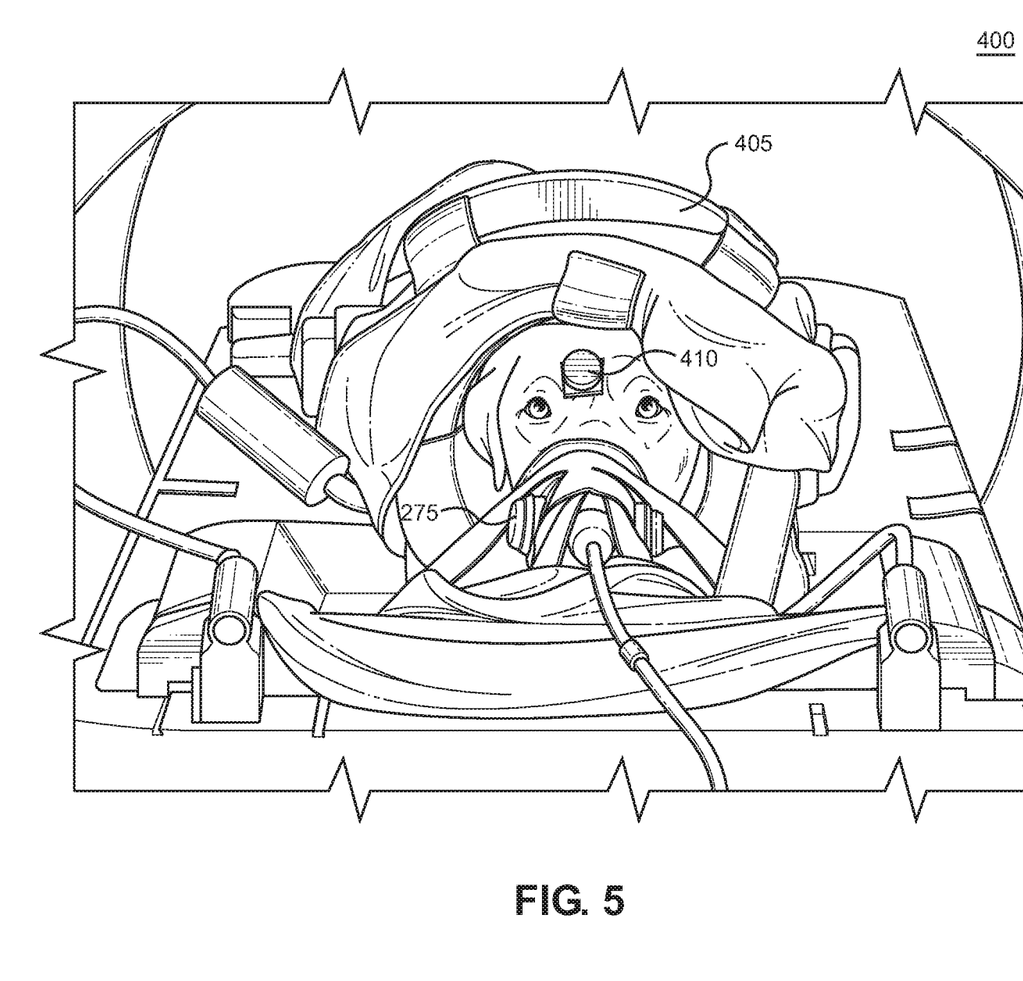
FIG. 5 is a graphical illustration of an embodiment of a subject dog in a scanner of the present application.

FIG. 5 illustrates a black dog positioned with muzzle in mask 275 for odorant delivery. A dot reflector 410 is mounted to dog's head for motion tracking (which will be discussed below), and the knee coil 405 encompasses the dog's head and the mask 275 is mounted on the front frame of the knee coil 405.

Optical Head Motion Tracking

One approach to head motion tracking is to independently record motion parameters during the scan, and then retrospectively use it to correct for motion or as a regressor of no interest in the activation analysis using a general linear model. This method is more ecologically valid, so the system of the present application, an optical head motion tracking system is utilized based on a single camera to monitor and record motion parameters. The advantages of single camera system over multi-camera systems are as follows. First, the former does not need calibration of the angle and settings between the cameras, which must be routinely and repeatedly established in the daily function of the MRI facility. Second, the former avoids the technical difficulty of mounting multi-camera systems in-bore. Third, many MRI bores limit the field of view of cameras and this narrow aperture hinders the placement and efficacy of the second camera.

Referring to FIGS. 2 and 5 simultaneously, the single camera optical head motion tracking system of this embodiment utilizes an MRRA Inc. model HT-1000 including of an IR (infrared) illuminator 140, an optical IR camera 135 with a built-in DSP processor, a dot reflector 410, a video monitor 145 and a palmtop computer 130. The IR illuminator 140 provides an IR source that is reflected by the dot reflector 410 mounted on the dog's head; the IR camera 135 picks up the reflected IR light from the dot reflector 410 and aids in calculating the change in dot position. Specifically, the image taken by the IR camera 135 is binarized so that the round dot reflector 410 is clearly separated from the background. The binarized image, the x, and y displacement of the centroid of the dot reflector 410 as well as its area calculated by the DSP processor in the IR camera 135 are digitally transmitted to the video monitor 145 and palmtop computer 130. The sampling rate is 1 kHz. By doing so, the time series of the x, y coordinates is obtained and the area in units of millimeter and $mm^2$, respectively. Then, these time series are downsampled to fMRI temporal resolution of TR (repetition time)=1 s, and the relative displacements of $x(t)$, $y(t)$ with respect to $x(0)$, $y(0)$, which were the x, y coordinates corresponding to the first fMRI volume, are obtained and used as a regressor of no interest in the activation analysis, after correcting for motion using image transformation based realignment. The dot reflector 410 in this embodiment is a one-inch diameter disk of engineering grade-10 retro-reflective tape (3M Corp.) attached by adhesive to the forehead of the dog. The video monitor 145 allows the operator to check for proper image framing.

The system described above is capable of 2-dimensional tracking, in the x and y directions. However, with a properly designed 3D target and scanner interface, prospective online motion correction may be performed with animals which cannot be trained to minimize head movement.

System Implementation Technical Objectives

The technical objectives of the system implementation the present application involve using a large sample of canines.

Functional imaging of awake dogs during olfactory stimulation: Given that outstanding service/working dogs require to have a desirable response to discriminative (an odor in the presence of which a dog has learned to make some behavioral response) as opposed to non-discriminative odors, the canine brain regions are investigated to determine which are differentially more activated to discriminative than non-discriminative odors.

Functional imaging of awake dogs during stimulation with emotional faces of human trainer: Dogs which are able to better respond to human emotions are likely to be more suitable to become therapy dogs for soldiers with post-traumatic stress disorder (PTSD). Keeping this in mind, awake dogs are shown human faces with neutral, negative and positive emotions obtained from the dogs' trainer/owner. Compliance to the task by the dogs are assessed using an MR compatible eye-tracker. Canine brain regions activated by negative and positive emotions compared to neutral emotions are then assessed.

Functional imaging of awake dogs during resting state: Resting state fMRI connectivity has been previously shown to be correlated with many behaviors such as cognitive abilities, attention, and memory retrieval in humans. The present application shows that capabilities and traits in dogs can be predicted from their resting state connectivity as well. This provides an endophenotype for selecting outstanding service dogs using a resting state scan. The system of the present application investigates the connectivity patterns associated with the dog's posterior cingulate cortex or frontal cortex (relevant to traits and capabilities), caudate nucleus (relevant to reward and reinforcement learning) and amygdala (relevant to empathy and emotional reactivity) in resting state.

Correlation of canine behavior with imaging metrics: Four behavioral measured are derived: (i) An integrated behavioral score is derived from the following canine behaviors: hunting, retrieving, and environmental soundness, (ii) A behavioral metric based on the ease with which dogs could be trained to hold their head still during an MRI scan is derived based on how readily they learn the routine in a mock scanner, acclimate to an actual MRI, time to first successful scan, and amount of effort (remedial training and successful scans/scans) to obtain useful scans, (iii) A behavioral metric based on an object-choice task assessing the dogs' sensitivity to human gestural communication, and (iv) A behavioral metric which measures empathic-like responses from dogs. The first two behaviors are more relevant to working dogs and the latter two to therapy dogs. The behavioral metrics described above are correlated with the following metrics: (a) The magnitude of activation to discriminative odors in brain regions which show a higher response to discriminative as compared to non-discriminative odors, (b) The magnitude of activation in brain regions showing increased response to negative and positive emotions as compared to neutral emotions, and (c) The magnitude of voxel-wise functional connectivity with the posterior cingulate cortex, frontal cortex, caudate nucleus and amygdala during rest. This identifies imaging metrics which co-vary with behavioral performance in canines.

Figure 7:
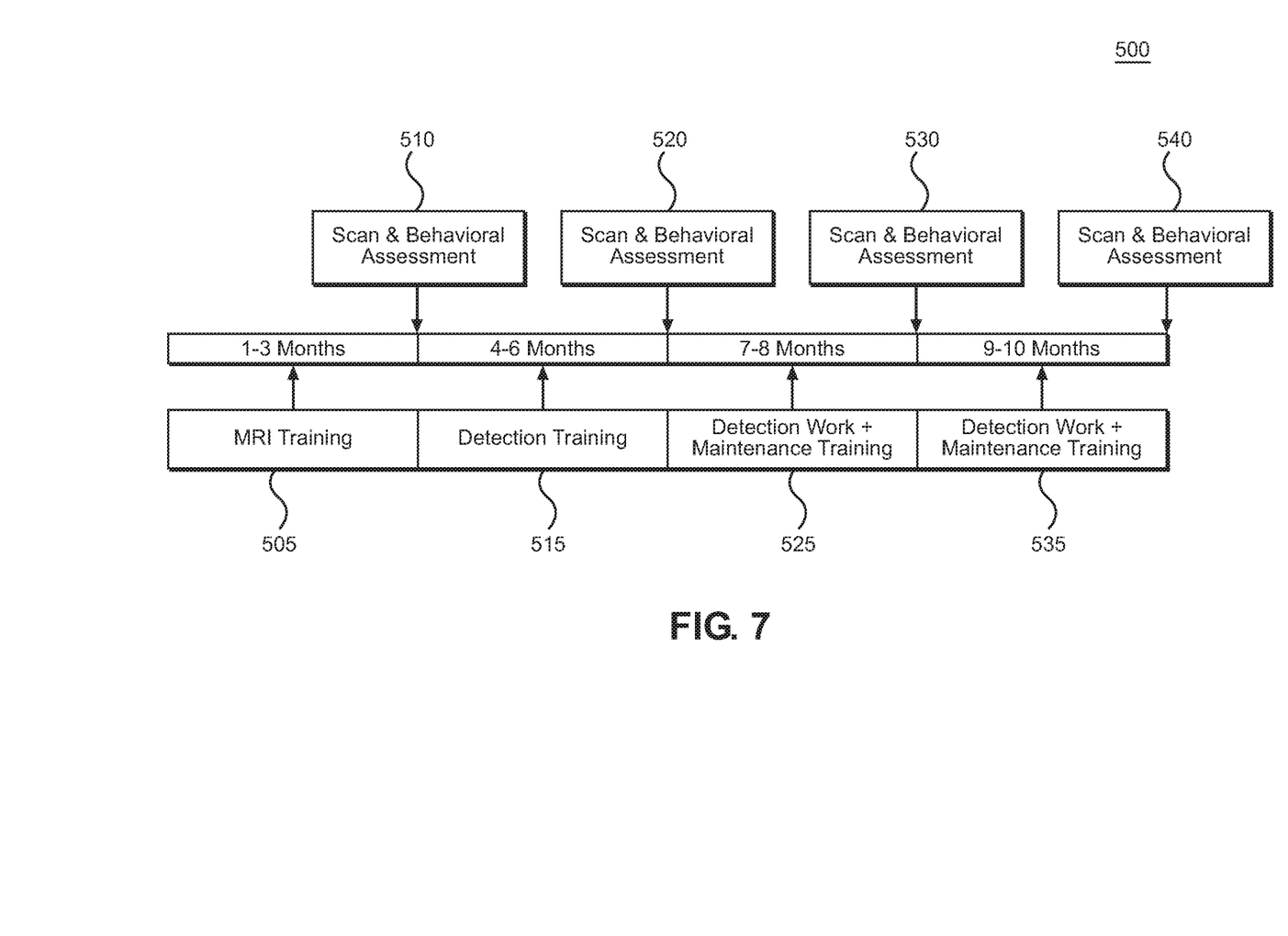
FIG. 7 is a schematic diagram illustrating an embodiment of a longitudinal method of the present application.

Longitudinal assessment: In order to identify metrics from functional imaging which could potentially be used to select highly-trainable work and therapy dogs, longitudinal assessment of brain and behavioral changes with training is warranted. In order to address this issue, experiments/ analyses enumerated above are performed in a large sample at four time-points 510, 520, 530, and 540: (i) After the dogs are trained to keep their head still during MRI data acquisition (referred to as MRI training), but before the start of training to become detector dogs (referred to as detection training), (ii) MRI trained awake dogs after completion of 3 months of detection training, (iii) MRI trained awake dogs 2-months after the end of detection training and completion of 2 months of detection work, and (iv) MRI trained awake dogs 4-months after the end of detection training and completion of 4 months of detection work. The ability of imaging metrics derived from the odor, emotion and resting state experiments at the first time-point to predict behavioral performance as well as imaging metrics at future time-points are assessed. This assists in selecting those imaging metrics suitable for screening dogs before detection (or other work or therapy related) training, for identifying those that are more likely to be successful. Further, the durability of brain changes induced by detection (or other work-related) training are assessed at third and fourth time-points.

Experimental Design and Data Analyses $T_2$*-weighted functional images are acquired using a single-shot gradient-recalled echo-planar imaging (EPI) sequence for blood oxygenation level dependent (BOLD) contrast on a Siemens 3 Tesla Verio scanner. Two hundred temporal volume repetitions of 14 axial slices with 3 mm thickness are acquired using the following parameters: repetition time (TR)=1000 ms, echo time (TE)=29 ms, field of view (FOV)=192×192 mm², flip angle (FA)=90 degree, in-plane resolution 3×3 mm, in-plane matrix 64×64, and whole brain coverage. The exclusion criterion for data are: 0.10 mm displacement between two consecutive acquisition time points in x, y or z direction. Also, in the z direction, if there is 10 mm total displacement between any two acquisition time points in one run, it meant that the dog's nose is not fully inserted in the mask at some time. This would jeopardize the neural effect at that time point. Therefore, any runs with 0.10 mm total displacement between any two acquisition time points in the z direction are also discarded. Anatomical images are acquired using magnetization-prepared rapid gradient echo (MPRAGE) sequence for overlay and localization, with parameters as: TR=1550 ms, TE=2.64 ms, voxel size: 0.792×0.792×1 mm³, FA=9 degrees, and in-plane matrix 192×192, FOV=152×152 mm², number of slices: 104.

The procedure for functional imaging of awake dogs during olfactory stimulation (relevant to working dogs) and resting state were described before. Here a new emotion regulation task and related behavioral assessments are described, which are relevant to identifying therapy dogs.

Functional Imaging of Awake Dogs During Stimulation with Emotional Faces of Human Trainer It should first be noted that the behavioral capabilities of dogs for processing emotional content in human faces is quite unique among mammals. The system and method of the present application illustrates that dogs possess specialized brain structure for processing human faces in their ventral visual stream (akin to the fusiform face area in humans). Further, it is also illustrated that increased reactivity of the amygdala during processing positive and negative human faces by dogs as compared to neutral human faces.

In one embodiment of the system and method of the present application, pictures of trainers/owners are taken using a high-end SLR camera with a uniform background, a front view and presented with a straight gaze and no obvious lateralized facial marks. In this embodiment, these images are processed in Adobe Photoshop in order to: convert them into grayscale images, and normalize luminance, contrast and brightness. Pictures of each trainer/owner depicting a range of neural, positive and negative emotions are developed using known methodologies. These pictures are then incorporated into a rapid event-related fMRI paradigm wherein the dogs are shown neutral, positive and negative emotional faces in random order for 4 seconds. The durations of an inter-trial interval, during which the dogs are presented a dark blank screen, are randomized with randomizing software.

Figure 6:
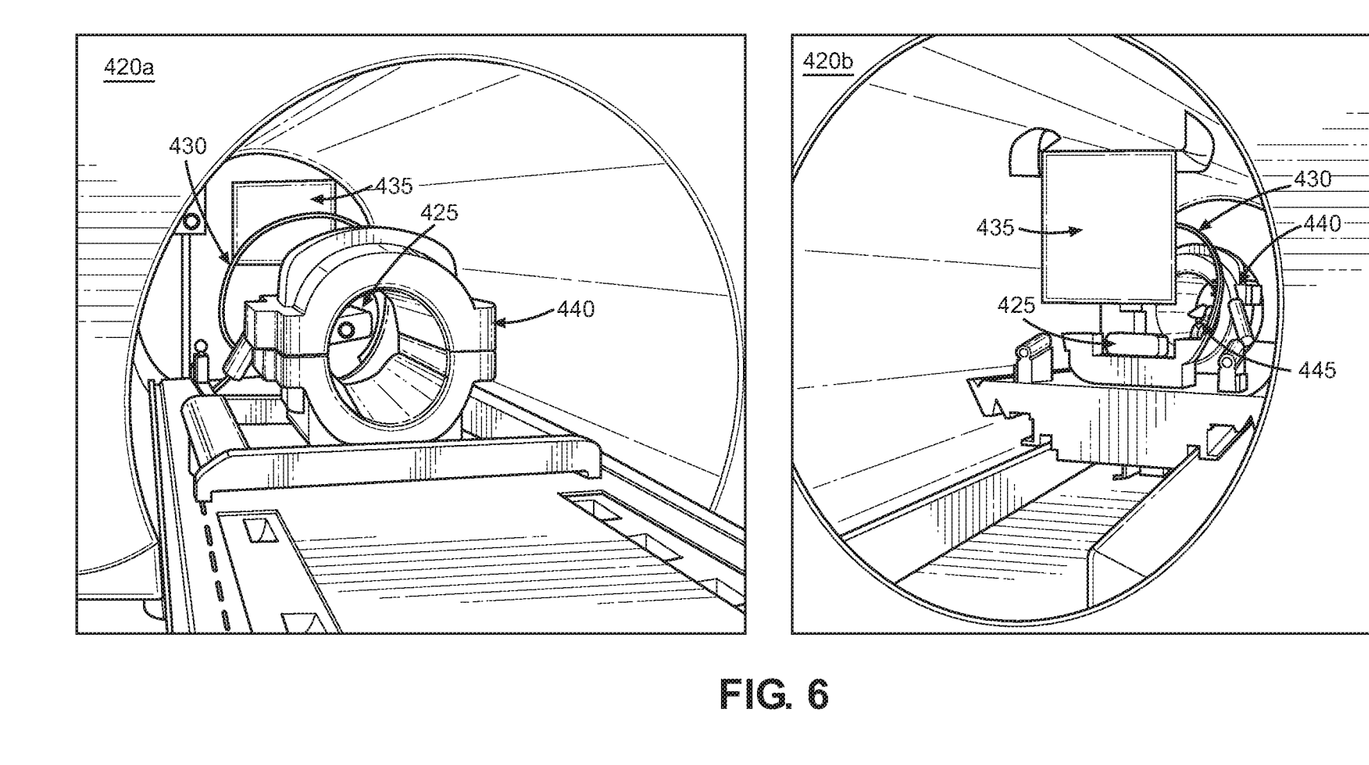
FIG. 6 is a graphical illustration of an embodiment of an eye tracking system of the present application.

An illustration of an embodiment of an eye tracking system 420 of the present application. The left illustration of the system 420*a* illustrates a front view showing the screen 435, dog head coil 440 and eye-tracker 425. The right illustration of the system 420*b* illustrates a rear view showing the screen 435, eye-tracker 425, and an awake and unrestrained dog 445 inside the dog head coil 440.

The MR-compatible eye-tracker system 420 is used with the following considerations. First, the compliance of the dog 445 has to be ensured during the task, in other words, one has to make sure that the dog 445 is actually looking at the pictures of emotional faces. Such a task which involves an active response from the dog, should employ eye-tracking to ensure compliance.

In one embodiment, an EyeLink 1000 Plus, which is an MR-compatible eye-tracker is employed. Referring again to FIG. 6, the system 420 for awake dog imaging is illustrated while they are viewing a screen 435 capable of displaying desired pictures (emotional faces in this case). The eye-tracker 425 is placed in between the dog head coil 440 and the screen 435 while the same setup is illustrated in 420*b* from the rear side of the scanner with an actual awake and unrestrained dog 445 placing its head inside the coil 440. The dog 445 can see through the infra-red (IR) reflector 430 into the screen 435. The IR reflector 430 beams infra-red rays from the base of the eye-tracker 425 to the dogs' 445 eye. IR rays bounce back from the dogs' 445 eye into the reflector 430 which then beams it into an IR camera at the base of the eye-tracker 425 due to the angle of the reflector. The IR camera then transmits this information into a laptop in the scanner control room via fiber optic cables. The data is then post-processed in order to determine the position and movements of the dogs' 445 eye. It can be seen from FIG. 6 that the eye-tracker can be easily incorporated into the MR experimental setup.

The fMRI data is first pre-processed and a general linear model (GLM) is constructed. Explanatory variables of the design matrix are derived for each of the three conditions—neutral, negative and positive pictures of the trainer—such that the corresponding boxcar function will have a value of 1 during the event and zero elsewhere. Other explanatory variables are also included such as time and dispersion derivatives and motion parameters. Individual subject t-maps are obtained contrasting facial pictures of positive and negative emotions with that of neutral emotions. They are then subject to a second-level random-effects analysis in order to derive group activation maps.

Momentary (direct) measures of attention are derived from the following properties of eye-tracking data:

Fixations: Stationary eye orientation on a target cell (pixels within the human face).

Saccades: Brief rapid eye movements between fixations.

Pupil dilation: Increase in the diameter of the size of the pupil.

Gaze duration: Time (ms) spent viewing a target cell or components of the cell (includes all instances of target cell fixations).

Regressions: eye movement with fixation back to a previously viewed target cell.

If it is found that the dog 445 was not looking at human faces during any trial, then the corresponding trial is excluded from activation analysis. Further, eye-tracking data is analyzed to test the hypothesis that emotional valence in human faces will modulate differences in laterality of eye movements in dogs.

Behavioral Assessments of Canine Social Cognition

These behavioral metrics are specifically relevant for identifying therapy dogs. First, a behavioral metric based on an object-choice task assessing the dogs' sensitivity to human gestural communication is employed. Next, a behavioral metric which measures empathy-like responses from dogs is used. This metric is adopted to measure the dogs' empathetic behavior. The neural correlates of both the behavioral measures discussed above assists in the understanding of the dogs' social cognition and their suitability to become therapy dogs.

Longitudinal Assessment

Referring to FIG. 7, a longitudinal assessment method 500 is illustrated. Ideally, the changes in functional imaging metrics with time are tracked. The dogs are trained in step 505 for awake, unrestrained fMRI, and are scanned in step 510 prior to undergoing training for detection work in step 515. At the conclusion of a standard 3-month course of training for detection work in step 515, and after 2 subsequent months of intermittent detection work and maintenance training in step 525, and after another 2 subsequent months of intermittent detection work and maintenance training in step 535, a scan and behavioral assessment 520, 530, 540 is conducted. The dogs are scanned in an awake state at each time point 510, 520, 530, 540, and changes in neural olfactory response to discriminative odors, neural response to positive/negative as compared to neutral human facial emotions and resting state functional connectivity of brain regions with posterior cingulate, caudate and amygdala seeds, with training are tracked. Further, behavioral assessments are carried out at each time point 510, 520, 530, 540.

Figure 8:
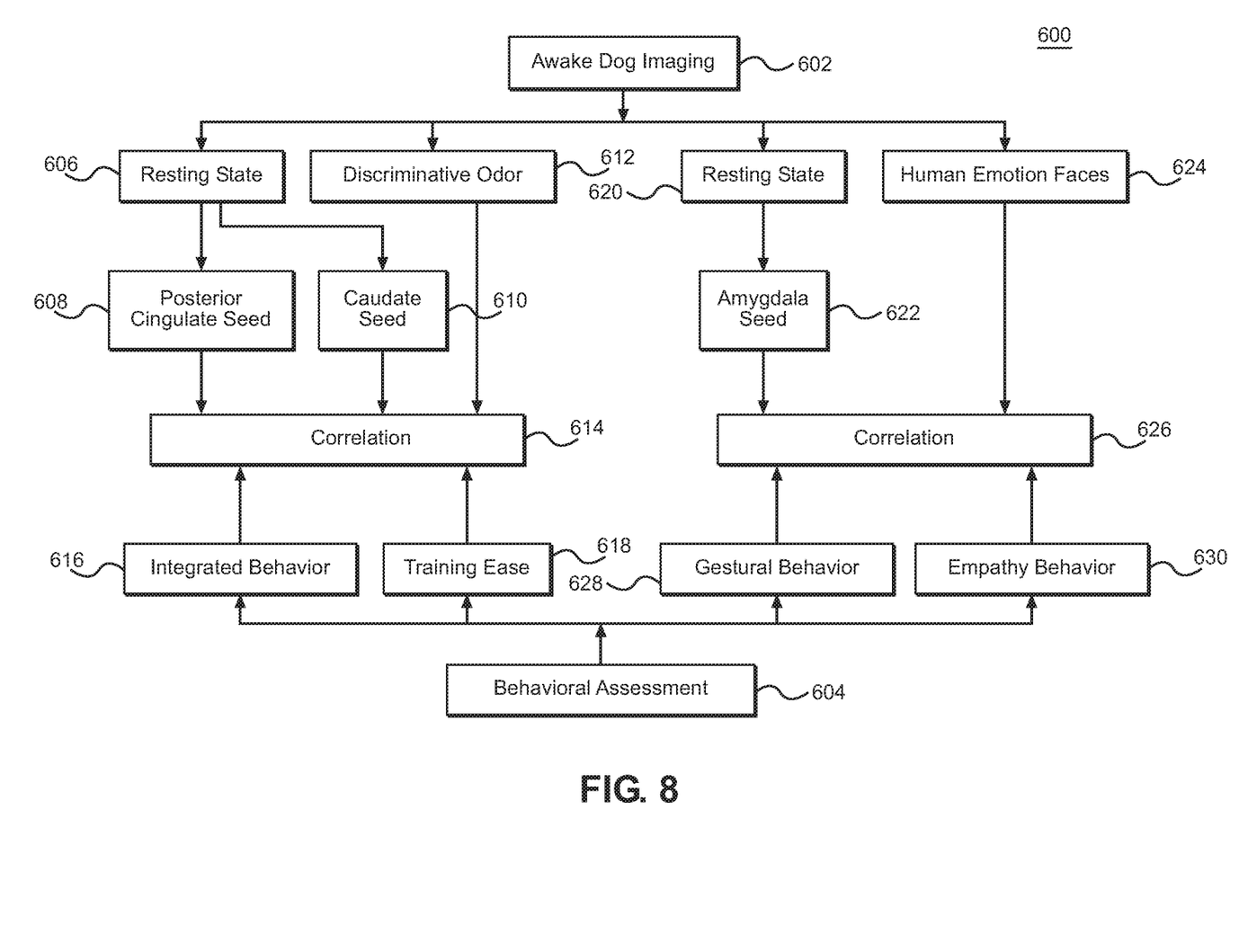
FIG. 8 is a schematic diagram illustrating an embodiment of a correlation method of the present application.

Referring now to FIG. 8, a correlation schematic 600 is illustrated. Correlations 614, 626 are carried out between imaging metrics 602 and behavioral metrics 604 within each time point 510, 520, 530, 540, as well as between time points 510, 520, 530, 540. Specifically, imaging metrics 602 derived from resting state 606 functional connectivity with posterior cingulate 608 and caudate seeds 610 as well as increased activations to discriminatory (as compared to non-discriminatory) odors 612 are correlated 614 with integrated behavior 616 and training ease 618. On the other hand, imaging metrics 602 derived from resting state 620 functional connectivity with amygdala 622 and increased activations to emotionally salient human faces 624 (as compared to neutral human faces) are correlated 626 with social, gestural behavior 628 and empathetic behavior 630 in dogs.

Figure 9:
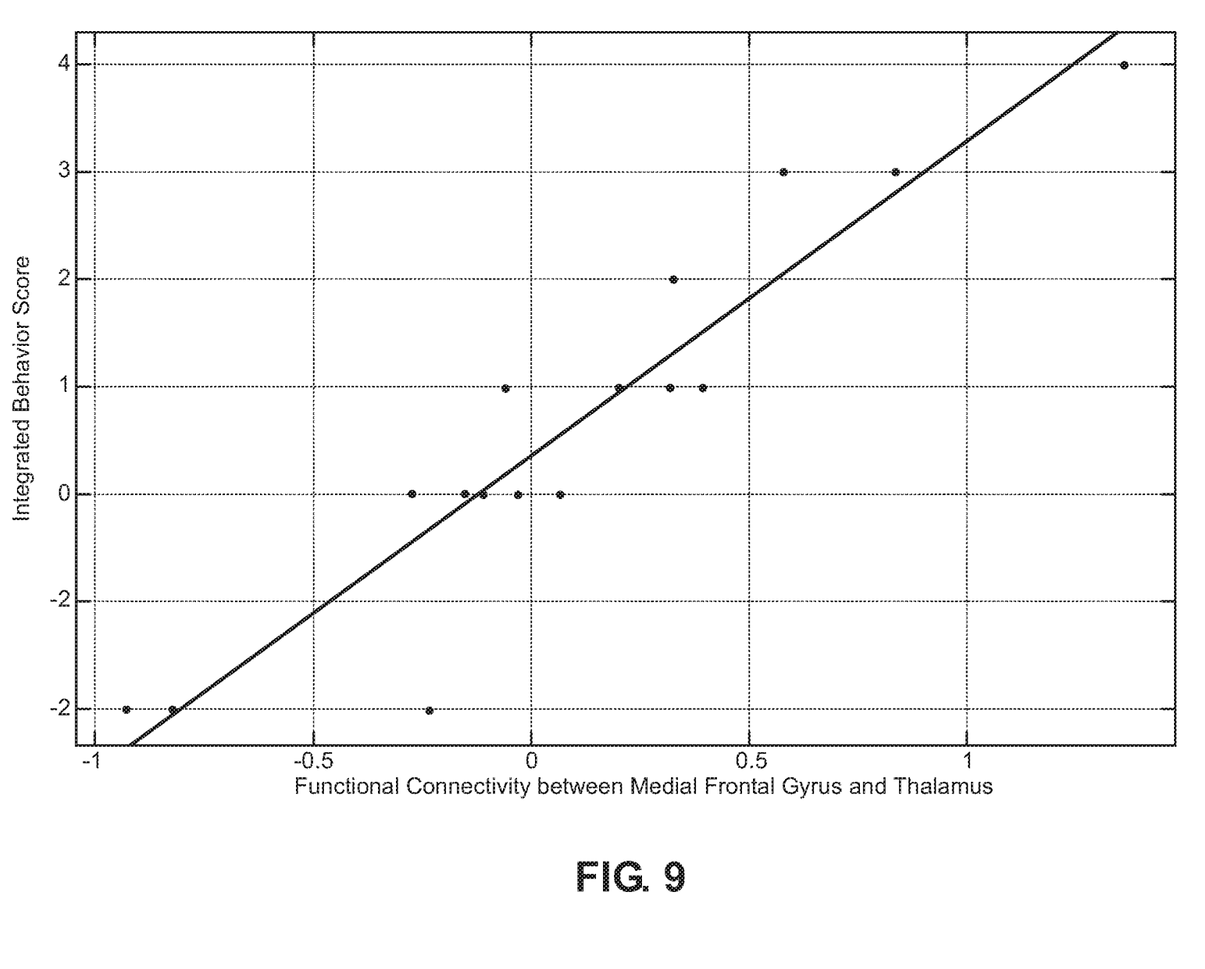
FIG. 9 is a graphical representation illustrating the correlation between integrated behavior and brain connectivity of an embodiment of the present application.

Referring to FIGS. 7 and 8, baseline resting state 606 functional connectivity prior to detection training 515 predicts behavioral performance at future time points. Specifically, baseline functional connectivity with posterior cingulate (or frontal cortex) 608 and caudate 610 predicts integrated behavior 616 and training ease 618 at future time points. One such example from acquired data is provided in FIG. 9. Here, the black dogs represent the dogs (16 in total), the x-axis represents the magnitude of functional connectivity between two brain regions—the medial frontal gyrus responsible for traits and capabilities and the thalamus which is a general conduit and control center in the brain—for each of those 16 dogs and y-axis represents the integrated behavioral score. A higher value of behavioral score is desirable and hence it can be seen that dogs with higher functional connectivity between these brain regions had better behavior. The value of correlation between brain connectivity and behavior is 0.93, brain connectivity explains 87% of the variance in behavior in the sample and their relationship is statistically significant with a p-value of $1.1 \times 10^{-7}$. This indicates that brain's functional connectivity in canines can be used as an endophenotype (or objective marker) of their behavioral performance. Baseline functional connectivity with amygdala 622 predicts social 628 and empathetic behavior 630 in dogs at future time points. This provides a way of selecting outstanding service dogs by just performing a resting state 606, 620 scan at recruitment.

Resting state 606, 620 functional connectivity, and neural response to olfactory 612 and human facial 624 emotional stimuli in dogs after initial detection training is a better predictor of behavioral performances at future time points, i.e. connectivity (and neural response to discriminative odors 612 and human emotional faces 624) from dogs after initial training better predicts behavior at future time points than connectivity of dogs prior to detection training.

Changes in resting state 606, 620 functional connectivity, neural olfactory response to discriminative odors, neural response to emotional human faces 624 and their predictive value with respect to behavior 604, persists at time points beyond scanning after initial detection training 515. This assumes that initial training is sufficient to create relatively intransient neural changes.

Additionally, olfactory response to a newly discriminated odor at each scan time point 510, 520, 530, 540. That is, the dogs are trained to make a new odor discrimination near the end of the standard course of detection training 515 and present that odor during olfactory fMRI scanning and subsequently introduce a new odor discrimination just prior to scanning at 2-months post initial detection training 515 and another new odor discrimination again at 4-months post initial detection training 515. There is no difference in olfactory response to newly learned discriminative stimuli at these different time points as well as to a control odor to which the dogs were initially trained to discriminate at the beginning of detection training 515. This suggests that initial detection training 515 results in a "learning to learn" phenomena with regard to odor discrimination that makes learning subsequent odor discriminations a relatively automatic process because connectivity patterns for such learning have already been established.

Detection Training

The dogs undergo standard explosive detector dog training in preparing dogs to be employed or sold as fully trained explosive detection dogs. This course of training is approximately 12-weeks long divided equally into an initial (or so-called pre-training) and operational training phase. It includes training the dogs to discriminate multiple explosive target odors ("imprinting") and progressive training in searching for target odors across varied and increasingly challenging operationally relevant scenarios. Because there are mastery-based criteria for moving from one stage of training to the next and for a dog successfully completing the course, the time varies slightly depending upon dog performance, weather, and staffing.

Ongoing Operational Searching and Maintenance Training

To provide a context similar to that of actual working dogs, the dogs are engaged in operational style searches and maintenance training after completing initial detection training. The dogs are taken out at least two days a week into live setting and perform search activities. There are no target odor hides on most of these searches, making the context similar in nature to that of actual working explosive detection dogs. Occasionally (no more than once per week), a target odor hide is placed in such scenarios. Actual working explosive detection teams will place out a target odor in a work setting to provide for a so-called motivational aid to maintain the dog's vigilance in searching. Similar to the typical work cycle of actual explosive detection teams, one day every other week, maintenance training is conducted with dogs. Maintenance training typically includes some short and simple odor recognition trials to provide the dogs contact with target odors and ensure that they are alert to them and one or two operationally relevant searches to maintain and assess the dogs' performance.

Behavioral Measures

To provide a behavioral rating with which to compare resting state brain activity, the initial procurement/breeding selection evaluation to test the potential of dogs for being successfully trained and employed as working detection dogs is used. This evaluation is used for determining whether to purchase a dog or enter a dog from a breeding program into detector dog training as well as to select dogs with superior potential as working dogs for breeding purposes. This evaluation is similar to and consistent with that used by the U.S. Military and most major U.S. Federal Agencies, such as the Transportation Security Administration, for the assessment of potential single-purpose detection dogs.

Correlation between activation magnitude in the odor task and integrated behavioral score for all brain regions which were more activated for discriminative as compared to non-discriminative odors. The $R^2$ value indicates the amount of normalized variance in behavior explained by activation.

The evaluation has two components: A component in which propensities of the dog related to success in being trained for detection work are assessed and; a component in which the ability of the dog to deal with and work effectively amidst varied environmental stressors is assessed. The training component primarily assesses the dog's propensity to retrieve and hunt using its nose and within these activities how easily the dog is distracted from these activities. The environmental component has 4 dimensions: Reaction to people/crowds, comfort moving about on varied surfaces and stairs, visual startle, and auditory startle. The evaluation itself has multiple exercises for each of the training and environmental dimensions. For example, there are 6 total hunt exercises, 3 in an outdoor setting and 3 in an indoor setting, each scored across a 5 point scale.

The evaluation of the dogs used in system development experiments were conducted as part of the normal commercial training activities rather than specifically for the purpose of system development experiments. Evaluations of dogs are conducted by senior working dog training professionals. To simplify the performance measures for use in correlating with resting state brain connectivity a composite score of 1 (low proficiency), 2 (medium proficiency) or 3 (high proficiency) was assigned for each of the following dimensions: Retrieve, Hunt, and Environmental Soundness. Finally, the scores of all dimensioned were added to obtain an Integrated Behavioral Score.

Another behavioral metric was defined based on the ease with which dogs could be trained (referred to as "training ease") to hold their head still during an MRI scan will be derived based on how readily they learned the routine in a mock scanner, acclimated to an actual MRI, time to first successful scan, and amount of effort (remedial training and successful scans/scans) to obtain useful scans.

Correlation between activation magnitude in the odor task and training ease behavioral score for all brain regions which were more activated for discriminative as compared to non-discriminative odors. The $R^2$ value indicates the amount of normalized variance in behavior explained by activation.

While embodiments presented in the disclosure refer to fMRI systems and methods for canines, additional embodiments are possible for other domains where assessments or evaluations are given for other purposes. In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. A method correlating imaging metrics and behavioral metrics of a subject canine, the method comprising:
   utilizing positive reinforcement to train the subject canine to assume a resting unrestrained and unsedated state during an imaging process;
   deriving from the resting unrestrained and unsedated state, awake imaging of the subject canine, a first set of brain functional connectivity metrics and a first set of increased activating metrics;
   deriving from a behavioral assessment, a set of integrated behavioral metrics and a set of training ease metrics, wherein the integrated behavioral metrics are derived from the subject canine's hunting and retrieving behaviors by assessing and rating the subject canine's propensity to retrieve and hunt using its nose and within these activities how easily the subject canine is distracted from these activities, and from the subject canine's environmental soundness behaviors by assessing and rating the subject canine's reaction to people and/or crowds, comfort moving about on varied surfaces and stairs, visual startle, and auditory startle, and the training ease metrics are derived from the ease with which the subject canine can be trained to perform a task;
   correlating the first set of functional connectivity metrics and the increased activation metrics with the set of integrated behavior metrics and the set of training ease metrics;

deriving from the resting state, awake imaging of the subject canine, a second set of functional connectivity metrics and a second set of increased activating metrics;

deriving from the behavioral assessment, a set of gestural behavior metrics and a set of empathy behavior metrics, wherein the gestural behavior metrics are derived from an object-choice task assessing the subject canine's sensitivity to human gestural communication, and the empathy behavior metrics are derived from measurements of the subject canine's empathetic behavior; and correlating the second set of functional connectivity metrics and the second set of increased activation metrics with the set of gestural behavior metrics and the empathy behavior metrics, wherein the correlating steps occur during and between a scan conducted on the subject canine during a longitudinal assessment, and further wherein the correlating steps are utilized to determine whether the subject canine will exhibit a high behavioral score during service training by correlating metrics derived from imaging with metrics derived from the behavioral assessment to predict behavioral performance during service training.

2. The method of claim 1, wherein the first set of increased activation metrics are derived from subjecting the subject canine to discriminatory odors.

3. The method of claim 1, wherein the second set of increased activation metrics are derived from subjecting the subject canine to emotionally salient human faces.

4. The method of claim 1, wherein the first and second sets of functional connectivity metrics include resting state functional connectivity derived between any given seed region in the brain and any other brain region of the subject canine, wherein the first set of functional connectivity metrics include at least a posterior cingulate seed and caudate seed.

5. The method of claim 4, wherein the second functional connectivity metrics include amygdala seed.

* * * * *